United States Patent [19]

Hanson et al.

[11] Patent Number: 5,354,330
[45] Date of Patent: Oct. 11, 1994

[54] HEART VALVE PROSTHESIS

[75] Inventors: Donald W. Hanson, Chanhassen; Richard W. Kramp, Arden Hills; Manuel A. Villafana, Minneapolis, all of Minn.

[73] Assignee: ATS Medical Inc., Plymouth, Minn.

[21] Appl. No.: 122,802

[22] Filed: Sep. 16, 1993

Related U.S. Application Data

[63] Continuation of Ser. No. 973,938, Nov. 10, 1992, abandoned, which is a continuation of Ser. No. 786,253, Oct. 31, 1991, abandoned.

[51] Int. Cl.⁵ ........................ A61F 2/24; F16K 15/00
[52] U.S. Cl. ........................................ 623/2; 137/527
[58] Field of Search ............... 623/2, 3, DIG. 900; 137/521, 527, 527.8

[56] References Cited

U.S. PATENT DOCUMENTS

| | | |
|---|---|---|
| Re. 31,040 | 9/1982 | Possis . |
| 4,178,639 | 12/1979 | Bokros ........................ 623/2 |
| 4,225,980 | 10/1980 | Martinez . |
| 4,276,658 | 7/1981 | Hanson et al. . |
| 4,308,624 | 1/1982 | Klawatter . |
| 4,373,216 | 2/1983 | Klawitter . |
| 4,451,937 | 6/1984 | Kiawitter ..................... 623/2 |
| 4,601,719 | 7/1986 | Totten ......................... 623/2 |
| 4,605,408 | 8/1986 | Carpentier .................. 623/2 |
| 4,676,789 | 6/1987 | Sorensen et al. ............ 623/2 |
| 4,692,165 | 9/1987 | Bokros ........................ 623/2 |
| 4,808,180 | 2/1989 | Johnson ...................... 623/2 |
| 4,822,353 | 4/1989 | Bokros ........................ 623/2 |
| 4,863,459 | 9/1989 | Olin ............................. 623/2 |
| 4,872,875 | 10/1989 | Hwang ....................... 623/2 |
| 4,935,030 | 6/1990 | Alonso ........................ 623/2 |
| 5,002,567 | 3/1991 | Bona et al. .................. 623/2 |
| 5,061,278 | 10/1991 | Bicer .......................... 623/2 |
| 5,080,669 | 1/1992 | Tascon et al. ............... 623/2 |

FOREIGN PATENT DOCUMENTS

| | | | |
|---|---|---|---|
| 0050971 | 5/1982 | European Pat. Off. ........... 623/2 |
| WO01698 | 2/1991 | PCT Int'l Appl. . |
| WO02197 | 2/1992 | PCT Int'l Appl. . |

Primary Examiner—Randall L. Green
Assistant Examiner—Mary Beth Jones
Attorney, Agent, or Firm—Haugen and Nikolai

[57] ABSTRACT

An improved heart valve prosthesis arranged for permanent implantation to replace a defective natural heart valve, wherein the improved prosthesis device includes an annular body or ring designed to retain a pair of rotatable flat plate occluders. The structure of the present invention contains modifications which improve the flow dynamics therethrough, and reduce if not eliminate the formation of eddies or areas of stasis in and along the flow pattern. The annular ring is provided with oppositely disposed pairs of spherical segments which form pivot areas for the occluders, with the occluders being provided with concavities engageable with the spherical segments. Stops are provided for controlling the degree of arcuate travel or rotational skirt of motion. The abutment surfaces are arranged at positions spaced from the axis of rotation so as to improve the distribution of stresses created during closure. The flow channel through the annular body or ring is designed to expand or flare outwardly from the flow inlet end toward the outlet end.

6 Claims, 4 Drawing Sheets

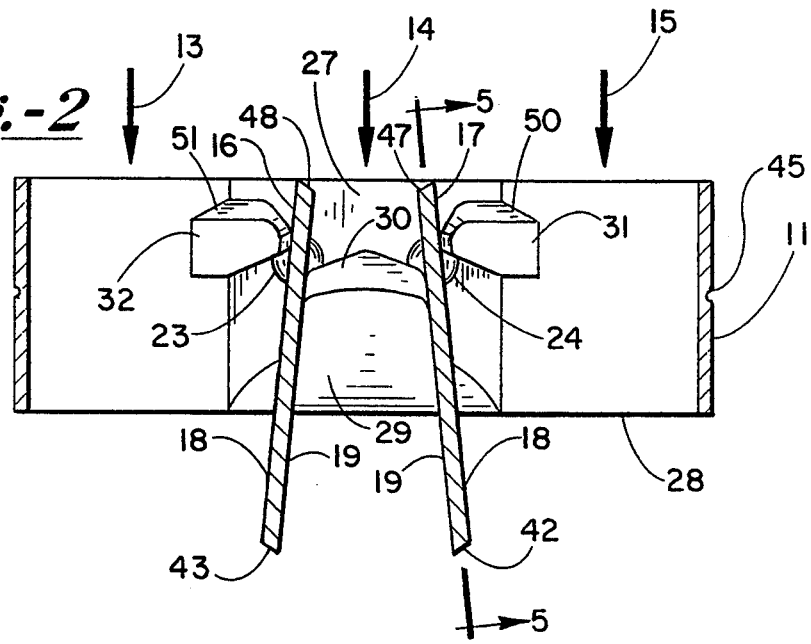
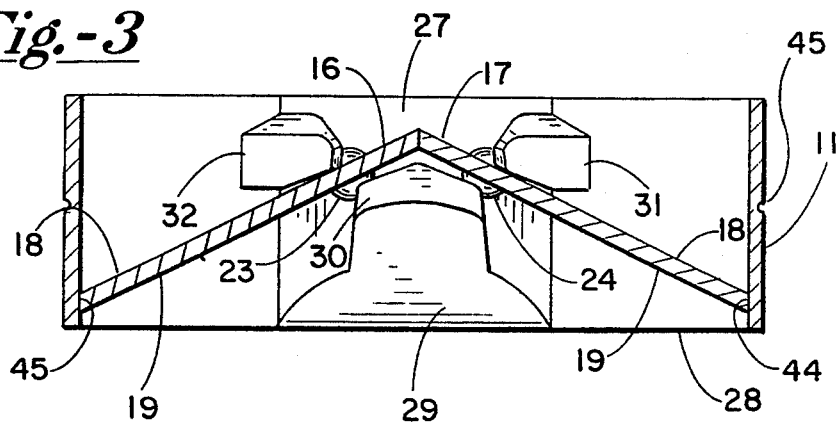
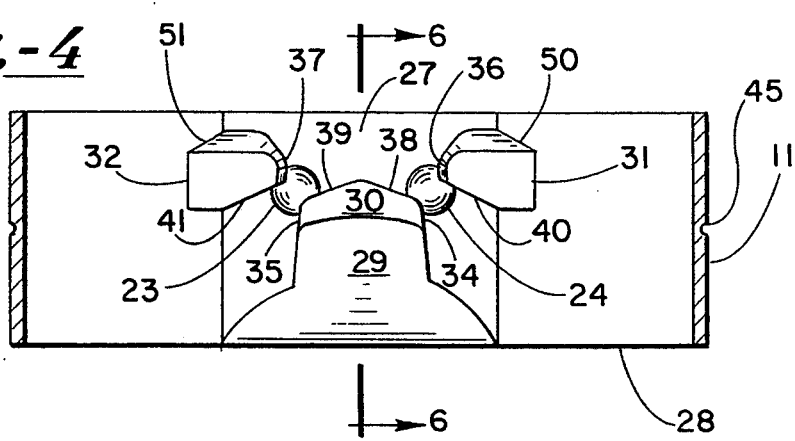

HEART VALVE PROSTHESIS

This is a continuation of application Ser. No. 973,938, filed on Nov. 10, 1992, now abandoned which is a continuation of copending application Ser. No. 786,253, filed on Oct. 31, 1991, now abandoned,

BACKGROUND OF THE INVENTION

The present invention relates generously to an improved heart valve prosthesis, and more particularly to such a prosthesis device which may be implanted to replace the defective natural heart valve. The improved prosthesis device of the present invention employs a pair of occluder means, each in the form of a flat plate, both functioning hemodynamically through periodic opening and closing motion which is created through normal pumping action of the heart.

The present invention is a modification of that certain heart valve prosthesis disclosed and claimed in U.S. Pat. Nos. 4,692,165, Bokros and 4,822,353, Bokros, with the structure of the present invention utilizing modified forms of pivot means, occluder stop means, internal configurations for the annular body or ring, all of which combine to provide modified forms of flow characteristics through the valve prosthesis. The structural configuration involved in the device of the present invention is designed to improve the flow dynamics and reduce areas of statis, and if possible, significantly reduce if not eliminate the formation of eddies in the flow pattern through the valve.

Prosthetic heart valves function essentially as check valves. Blood flow which occurs as a result of the natural pumping action of the heart causes periodic opening of the occluder means, with the system pressure closing the occluder means during periods of diastole when in the aortic position or during periods of systole when in the atrio-ventricular position.

A variety of prosthetic heart valves have been proposed and utilized in the past. Certain of these prosthetic devices have employed a caged ball arrangement which also function and control blood flow in response to the normal pumping action of the heart. Other heart valve prostheses have employed occluders in the form of either a round disc or a pair of semi-circular and semi-elliptical plates. The latter are normally referred to as bi-leaflet valves. While various materials of construction have been employed in the past, the more recently utilized heart valve prostheses have been fabricated essentially from pyrolytic carbon. The improved prosthetic heart valve of the present invention is a bi-leaflet valve fabricated from pyrolytic carbon.

Bi-leaflet heart valves normally employ pivot means to appropriately guide and otherwise control the motion of the leaflets through their transition from open disposition to closed disposition. In addition, means have been provided to control or limit the extent of motion to which the leaflets are subjected during opening and closing, thereby providing an arrangement wherein the motion of the individual leaflets is carefully guided, controlled, limited, and maintained.

It is known that blood components including those cells normally found in human blood are extremely fragile and delicate, and that these cells can be damaged and/or destroyed when subjected to unusual mechanical forces. Thus, care must be taken in order to control the nature of the forces created due to the occurrence of relative motion between the leaflets and the annular body. For example, reduction of the occurrences of rubbing contact between stationary and moving surfaces is of importance when such contact is likely to cause mechanical damage to the components or cells present in blood. The design and configuration of the heart valve prosthesis of the present invention is such that care has been taken to reduce the creation of zones or areas where blood passing through the device is exposed to substantial mechanical forces. In addition to damage due to mechanical forces, it has been found that constituents of human blood are subject to damage whenever any quantity of blood is retained or held in an area or zone of stasis or stagnation within a prosthesis. The design and configuration of the heart valve prosthesis of the present invention is such that areas of stasis are reduced, if not entirely eliminated.

SUMMARY OF THE INVENTION

The heart valve prosthesis of the present invention comprises a generally annular body member having an interior surface defining a central passageway for blood flow therethrough. The annular body member is provided with means for supporting a pair of pivotally movable leaflets or occluders within the annular body for alternately and periodically opening and closing, thereby allowing a unidirectional flow of blood through the passageway. The leaflets comprising the occluder means are provided with aligned, inwardly extending notches or cut-out zones providing concavities at opposed locations along the periphery. These concavities are arranged to mate with oppositely disposed pairs of inwardly projecting occluder supports or pivot areas in the form of spherical segments which extend convexly inwardly from opposed chordal locations within the annular body member. In this manner, the spherical segments form pivot areas or fulcrum points which engage and are received within the opposed aligned concavities. In this connection, the axes of the pivot areas are arranged along and generally coincidental with the axis extending between the concavities formed within individual leaflets. Stop means are provided which extend inwardly of the interior surface of the annular body member and cooperate with the pivot areas and the leaflets to control and otherwise limit the extent of pivotal motion of each leaflet during its opening and closing. The stop means are arranged to reduce the magnitude of forces created on the blood retained along and between the surfaces of the stop means and the individual leaflets.

In normal operation, the leaflets comprising the occluder means pivot about an axis extending between individual ones of opposed pairs of fulcrum points or pivot areas. While the individual abutment surfaces of the stop means provide relatively elongated zones or areas of contact, additional contact is achieved between the mating surfaces of the elliptical edges of the leaflets and the interior surface of the annular body. Additionally, areas of mutual contact exist during closure between the straight-line end zones of the individual leaflets. This utilization of areas of contact assists in reduction of mechanical forces to which the blood is exposed during normal operation of the prosthesis.

Therefore, it is a primary object of the present invention to provide an improved heart valve prosthesis means which may be fabricated from pyrolytic carbon, and which is designed to provide improved performance while responding hemodynamically to the normal pumping action of the heart.

It is a further object of the present invention to provide an improved heart valve prosthesis which is designed to reduce exposure of blood and its constituents to substantial mechanical forces and stresses, thereby reducing the likelihood of damage to constituents and cells found within human blood.

It is yet a further object of the present invention to provide an improved heart valve prosthesis with mechanical design features and characteristics which reduce the occurrence of a concentration of mechanical stresses at given locations in the device.

It is yet a further object of the present invention to provide an improved heart valve prosthesis which is designed to enhance the uniformity of flow through the device so as to substantially reduce the creation of zones of stasis or stagnation within the device and its environs.

Other and further objects of the present invention will become apparent to those skilled in the art upon a study of the following specification, appended claims, and accompanying drawings.

IN THE DRAWINGS

FIG. 2 is a vertical sectional view taken along the line and in the direction of the arrows 2—2 of FIG. 1;

FIGS. 3 and 4 are views similar to FIG. 2, with the leaflets being shown in the closed position in FIG. 3, and with the leaflets having been removed in the view of FIG. 4;

DESCRIPTION OF THE PREFERRED EMBODIMENT

Figure 1:
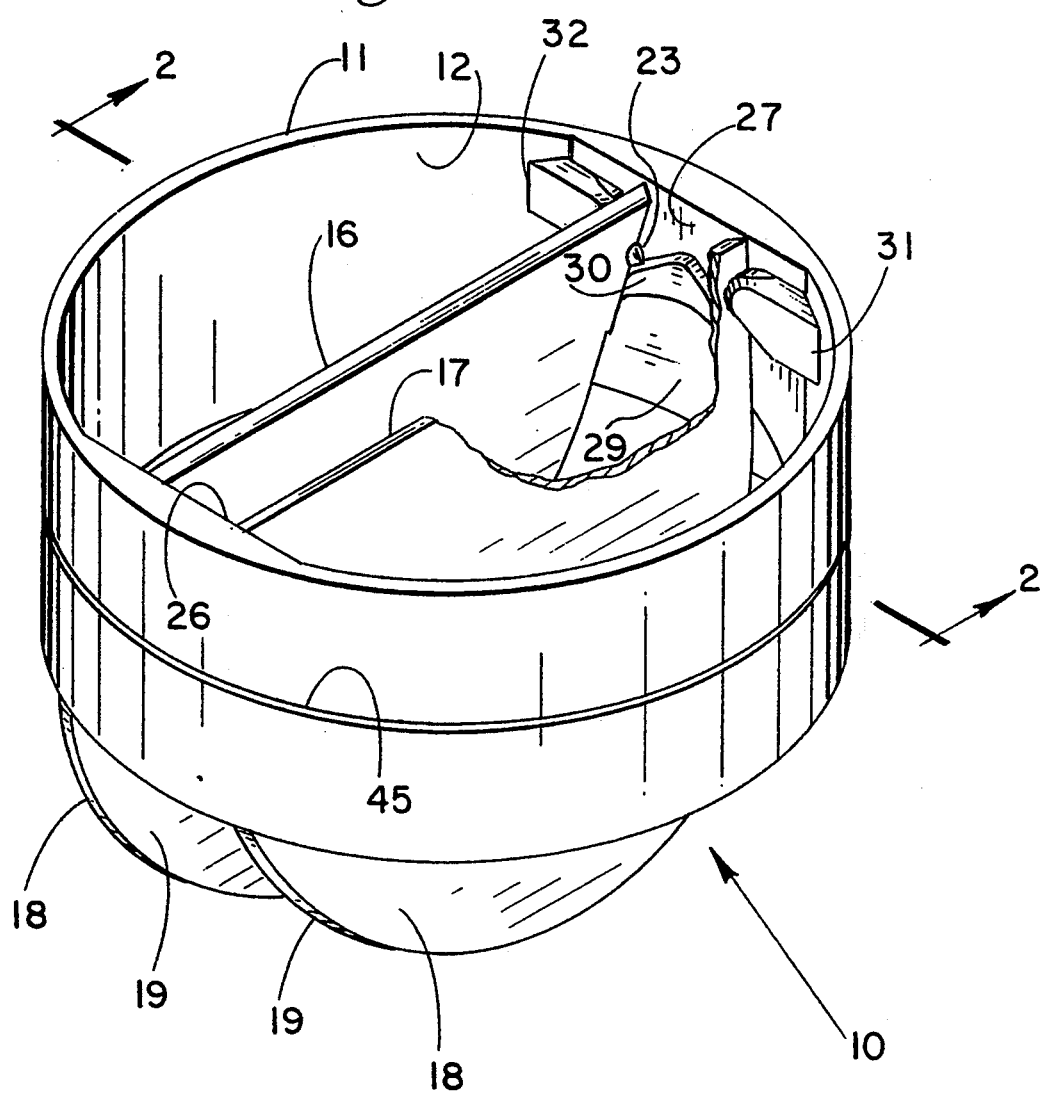
FIG. 1 is a perspective view of the heart valve prosthesis of the present invention, with the valve being shown from the inflow end, and shown with the leaflets in open position.

In accordance with the preferred embodiment of the present invention, and with particular attention being directed to FIGS. 1 and 2 of the drawings, the heart valve prosthesis generally designated 10 comprises a generally annular body member 11 having an interior surface 12 defining a central passageway for blood flow therethrough. With attention being directed to FIG. 2, the directional arrows 13, 14, and 15 illustrate the typical flow pattern for blood entering the inflow end and passing through the heart valve prosthesis 10, with portions of the flow occurring between the occluder members and the surface of the annular body member, and with further portions of the blood flow passing between the surfaces of the individual leaflets. Occluder means including leaflets 16 and 17 are provided, with the leaflets having upstream directed major surfaces 18—18, and downstream directed major surfaces 19—19. As indicated, the occluder means respond hemodynamically to the natural pumping action of the heart, so as to alternately open and close so as to permit flow of blood through the passageway upon occurrence of an increase in pressure on the inflow side so as to cause a positive pressure differential relative to the outflow side of the device. Closure occurs as the relative pressures become positive with respect to the outflow side.

Figure 5:
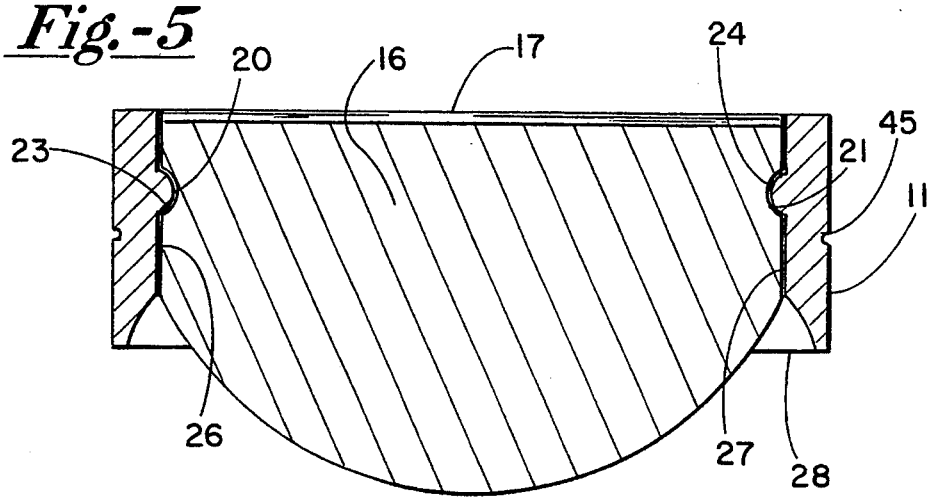
FIG. 5 is a vertical sectional view taken along the line and in the direction of the arrows 5—5 of FIG. 2.
Figure 6:
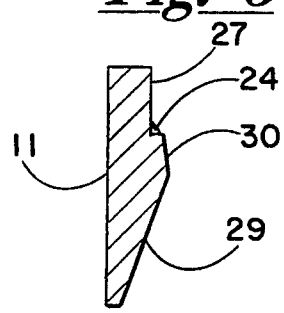
FIG. 6 is a vertical sectional view taken along the line and in the direction of the arrows 6—6 of FIG. 4, and showing one interior end of the heart valve prosthesis.
Figure 7:
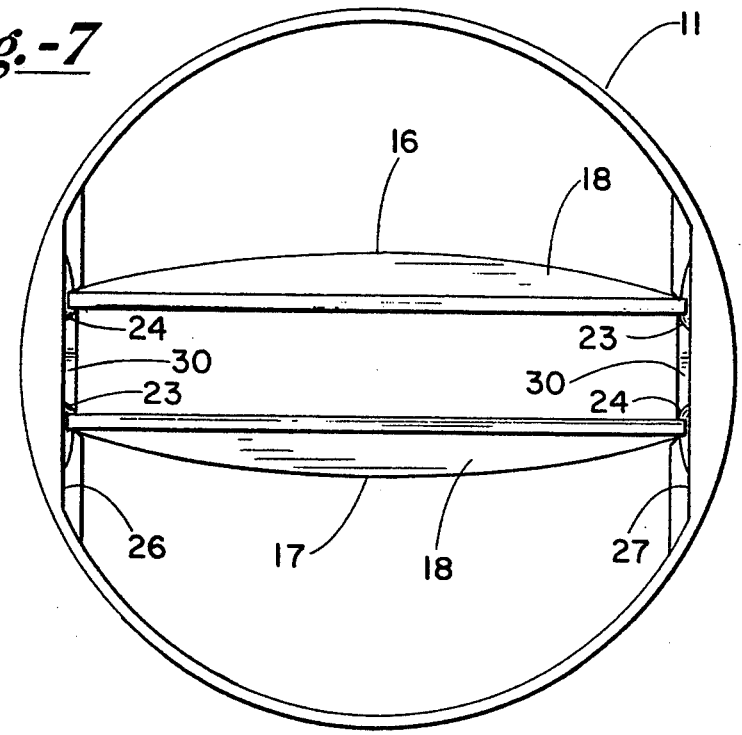
FIG. 7 is an inflow plan view of the heart valve prosthesis, with the leaflets being shown in the open position.

With attention now being directed to FIG. 5 of the drawings, each leaflet 16 and 17 is provided with aligned pairs of concavities, as at 20 and 21. It will be noted that leaflets 16 and 17 are substantially identical, one to another, with each being the mirror image of the other. Concavities 20 and 21 are designed along the edge surfaces to receive and capture pivot areas 23 and 24 therewithin, as illustrated in FIGS. 2 and 5. Specifically, the utilization of the spherical projections or pivot areas 23 and 24 reduces the area impeding blood flow, thereby providing an increase in the effective cross-sectional area available for flow through the body 11. The dimensional tolerances between the concavities 20 and 21 and the pivot areas 23 and 24 are such that little, if any, transitional movement of the leaflets 16 and 17 is permitted. The dimensional tolerances are typically such that a normal gap of about 0.001 inch exists between the outer surfaces of the pivot areas and the inner surfaces of the concavities, with this dimension being sufficient to accommodate free movement or flow without creation or generation of significant areas of stasis.

With continued attention being directed to FIGS. 2–4 of the drawings, a plurality of stop means are provided which extend inwardly of the oppositely disposed flat surfaces 26 and 27 (FIG. 1). These flat surfaces as at 26 and 27 are parallelly disposed inwardly facing surfaces which are formed generally along chordal planes of the interior surface of the annular body. These flat surfaces are tapered and/or flared outwardly in the direction of flow and toward the base of the body member 11 so as to become coincidental with and merge into the bottom end 28 (FIG. 2) of annular body member 11. The outwardly extending flared area in the flow direction and adjacent the outflow end is illustrated at 29 in FIG. 3. It has been found that this design arrangement improves flow and reduces stasis, and also reduces any tendency toward the creation of turbulent flow during the occurrence of normal blood flow and normal functioning of the heart valve prosthesis. Stop means such as shown at 30, 31 and 32 extend inwardly of the flat surfaces 26 and 27. The stop means are provided with relatively elongated abutment surfaces so as to control the extent of pivotal motion of each of the occluder means (leaflets) 16 and 17 so as to achieve opening and closing of the valve. The stop means are, as indicated, arranged laterally of the pivot areas, and thus achieve the function of limiting pivotal motion in opening and closing of the leaflets 16 and 17. Surfaces which contribute to limitation of opening of the leaflets are found at 34, 35, 36, 37, 40 and 41. Inasmuch as the forces being applied to the components of the valve during the periods of blood flow while the leaflets 16 and 17 are open are minimal, there is no compelling need for the creation of unusually elongated linear areas for further reduction of mechanical forces and stresses. In other words, blood damage is more likely to occur during that portion of the cycle when the leaflets of the heart valve prosthesis are closed. Furthermore, it will be noted that the stop means 34–37 inclusive provide for a substantial flow area through the body member 11, and in the direction and along the line of the arrow 14 (FIG. 2).

Figure 8:
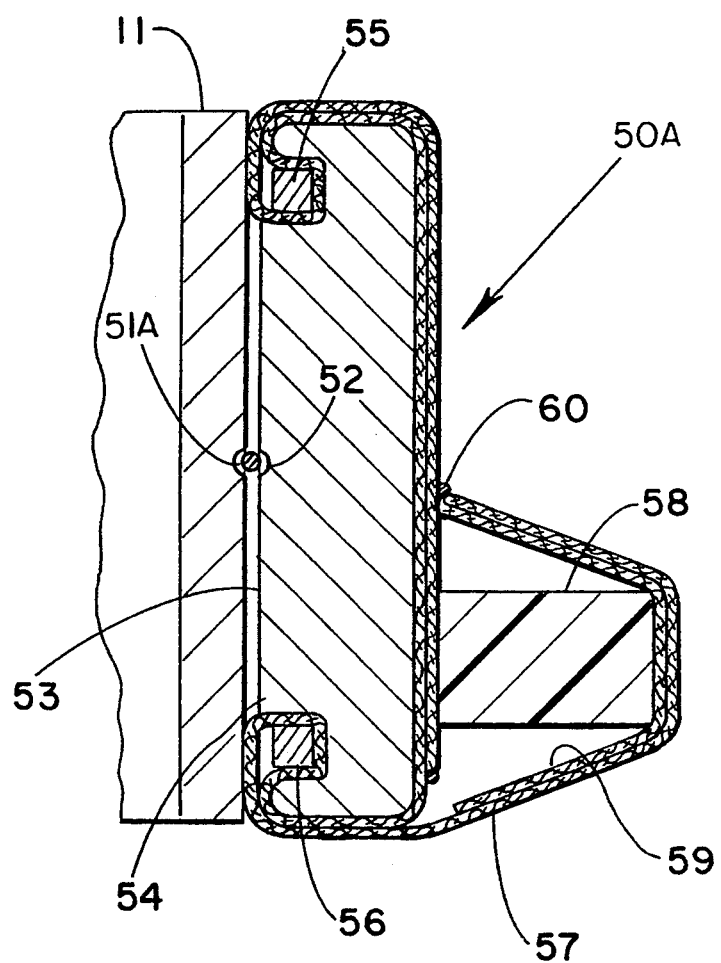
FIG. 8 is a fragmentary vertical sectional view taken through a portion of the annular body, and illustrating the detail of the sewing cuff assembly secured to the outer circumferential surface of the valve assembly, with FIG. 8 being shown on a slightly enlarged scale.

As indicated FIGS. 1–6 of the drawings, retaining lock wire accommodating groove 45 is provided on the outer surface of annular body 11. With particular attention now being directed to FIG. 8 of the drawings, the sewing cuff assembly generally designated 50A is shown mounted and secured in place on the outer circumferential surface of annular body member 11. This assembly comprises a lock wire 51A adapted to be received within groove 45 formed in annular body 11, as well as within groove 52 formed along the inner circumferential surface 53 of stiffening ring 54. A pair of lock rings 55 and 56 are provided for engaging and appropriately securing fabric 57 in place on assembly 50A. A filler ring 58 is provided within the confines of loop zone 59, with a suture being formed as at 60 to retain loop area 59 of fabric 57 in place on the overall assembly 50A. Typically, stiffening ring 54 and lock rings 55 and 56 are fabricated from a material such as titanium, with lock wire 51A being formed of a suitable blood-compatible, titanium-compatible metal. Fabric 57 may typically be prepared from a double velour material which is commercially available. Filler 58 may conveniently be fabricated from a suitably inert material such as polytetrafluoroethylene which is also commercially available. Stiffening ring 54 has a longitudinal groove formed medially thereof in order to receive an outwardly bent portion of lock wire 51A therethrough, thus serving to retain assembly 50A in tact and in place on the outer surface of annular member 11.

Additionally, it should be pointed out that sewing cuff assembly 50A retains valve assembly 10 in place by frictional engagement between the inner surface of fabric 57 and the outer surface of annular body member 11. When placing the valve assembly in place within the patient's system, sewing cuff 50A is secured in place, and the valve prosthesis 10 may then be rotated to a desirable orientation with respect to its implanted location. In other words, with this configuration, it is, therefore, possible for the implanting surgeon to suture the conventional tubular fabric or sewing cuff in place and thereafter rotatably orient the valve to its desired leaflet opening position after the tubular fabric has been appropriately secured in place.

When the valve leaflets are in their closed disposition, the leaflets 16 and 17 rest upon the abutment surfaces 38, 39, 40 and 41. Additionally, the outer tip portions of the leaflets 16 and 17, as at 42 and 43, are arranged in contact with the interior surface 12 of annular body member 11, as illustrated in FIG. 3 at 44 and 45. The straight-line edges of leaflets 16 and 17, as at 47 and 48 respectively are in abutting contact when the leaflets are closed. As indicated hereinabove, there is very little transitional movement of the leaflets 16 and 17 during normal functioning of the valve, with this motion being sufficient and adequate to contribute to a reduction in the mechanical forces being exerted upon mating and contact surfaces of the components within the valve. Specifically, there is only a relatively small amount of rubbing contact created between the rounded surfaces of the leaflets and the inner surface of the annular body 11, thus further contributing to a reduction in the forces exerted upon the components of the blood.

Attention is now directed to FIGS. 2–4 of the drawings, where the profiles of the individual abutment surfaces and stop means are illustrated. As indicated, the profile of the central stop, as at 30, includes an angularly inwardly projecting portion 30 together with an outwardly flared portion 29. The arrangement of stop means 31 and 32 are also illustrated, with the surfaces 50 and 51 being arranged angularly to the direction of flow of the blood. In this connection, the angle of surfaces 50 and 51 relative to the vertical flow axis is 45 degrees. However, it is noted that this angle may be increased to approximately 60 degrees while preserving the uniformity of flow through the body of the prosthesis.

Turning now to the operation of the heart valve prosthesis 10, upon the occurrence of the natural pumping action of the heart, when the inflow pressure exceeds the outflow pressure, thus causing flow of blood along the line and in the direction of the arrows 13, 14, and 15, leaflets 16 and 17 move or pivot to the open disposition. During the pressure reversal portion of the normal cycle, the leaflets 16 and 17 pivot to their closed disposition as illustrated in FIG. 3. Normal heart rhythm which is approximately 72 beats per minute for a human at rest, increases as a result of exercise or the like. In the open disposition, the leaflets are held at an angular disposition which is modestly less than parallel to the flow direction. Specifically, this angle of deflection from the axis of flow (the valve axis) is between about 4 degrees and 6 degrees, and preferably at about 5 degrees. For normal operation, a full 60 degree rotational skirt of motion is provided for the individual leaflets, thereby providing an angle of closure for the individual leaflets at about 25 degrees from a plane normal to the flow direction or annular valve body axis. Thus, a substantial number of cycles of the heart valve prosthesis is expected, and the components of the valve may be made from any suitable material that will resist wear when subjected to the virtually countless opening and closing movements of the occluder members of the valve. Pyrolytic carbon has been found to be a desirable material of construction for devices of this type. Furthermore, pyrolytic carbon has been found to be highly compatible with blood and its numerous components, is non-thrombogenic, without having presented problems from the standpoint of creation or generation of clotting activity.

Other modifications may be made to the device described hereinabove without actually departing from the spirit and scope of the present invention.

What is claimed is:

1. Heart valve prosthesis means comprising:
   (a) a generally annular body member having an interior surface defining a central passageway having a central axis for blood flow therethrough;
   (b) occlude means supported on said annular body for alternately blocking and then allowing the flow of blood through said passageway in a predetermined direction;
   (c) said occlude means having generally planar upstream and downstream major surfaces and being formed with aligned concavities at opposed locations along the periphery thereof;
   (d) a pair of opposed flat surfaces with parallely disposed inwardly facing surfaces formed along the interior surface of said annular body;
   (e) oppositely disposed pairs of spherical segments extending convexly inwardly from each of said flat surfaces of said annular body to form pivot areas engageable within said concavities formed in said occlude means with the axes of said spherical segments being arranged along and generally coincidental with the axis of said concavities;
   (f) first and second stop means extending inwardly of said flat surface and being disposed laterally of said convexly inwardly extending spherical segments and cooperating with said occlude means and pivot areas to control the extent of pivotal motion of each of said occlude means and to limit the extent of angular pivotal movement in the opening and closing of said occlude means, each of said first and second stop means including first and second abutment pad means;

(g) said first stop means comprising a radially inwardly extending abutment pad having in relation to a downstream direction and to said central axis an angularly inwardly flared profile surface at the upstream flow end and an angularly outwardly flared profile surface at the downstream flow end, and further having a pair of relatively elongated occlude opening contact surfaces arranged along the edge surfaces thereof and being disposed intermediate individual ones of said first and second pairs of pivot areas and with said occlude opening contact surfaces being arranged to contact the outflow surfaces of said occlude means to limit extent of angular opening thereof; and (h) said second stop means comprising a pair of laterally disposed abutment pads, each pad having in relation to a downstream direction and to said central axis an angularly inwardly flared profile surface at the upstream flow end thereof, each pad having a relatively elongated occlude closure contacting surface arranged along an edge surface of said angularly flared profile surface and with each abutment pad being disposed arcuately outwardly of said pivot areas for contacting the inflow surfaces of said occlude means to guide said occlude means and control the disposition thereof upon closure.

2. The heart valve prosthesis as defined in claim 1 being particularly characterized in that the occluder opening contact surfaces of said first pair of abutment surfaces are flared outwardly to maintain said occluder means at an angle of about 5 degrees from the flow direction.

3. The heart valve prosthesis as defined in claim 1 being particularly characterized in that said oppositely disposed pairs of spherical segments are substantially hemispherical in configuration.

4. The heart valve prosthesis as defined in claim 1 being particularly characterized in that said flared profile surfaces of said first and second stop means angularly intersect the axis of flow through said annular body member at an angle ranging from between 45 degrees and 60 degrees.

5. The heart valve prosthesis as defined in claim 1 being particularly characterized in that said flared profile surfaces of said first and second stop means angularly intersect the axis of flow through said annular body member, said angle of intersection is about 45 degrees.

6. The heart valve prosthesis as defined in claim 1 being particularly characterized in that said occluder means undergo a rotational skirt of motion between open and closed dispositions of about 60 degrees.

* * * * *